United States Patent [19]

Cannon

[11] Patent Number: 4,578,354

[45] Date of Patent: Mar. 25, 1986

[54] IMMOBILIZATION OF CATALYTICALLY ACTIVE MICROORGANISMS IN AGAR GEL FIBERS

[75] Inventor: John J. Cannon, Groton, Conn.

[73] Assignee: Pfizer Inc., New York, N.Y.

[21] Appl. No.: 492,780

[22] Filed: May 9, 1983

[51] Int. Cl.⁴ .............................................. C12N 11/10
[52] U.S. Cl. ...................................... 435/178; 435/837
[58] Field of Search ............... 435/174, 177, 178, 179, 435/182

[56] References Cited

U.S. PATENT DOCUMENTS

| | | | |
|---|---|---|---|
| 3,791,926 | 2/1974 | Chibata et al. | 435/109 |
| 3,957,580 | 5/1976 | Nelson | 435/180 |
| 4,138,292 | 2/1979 | Chibata et al. | 435/178 |
| 4,208,482 | 1/1980 | Ehrenthal et al. | 435/178 |

*Primary Examiner*—Robert J. Warden
*Assistant Examiner*—Cynthia Lee Foulke
*Attorney, Agent, or Firm*—Charles J. Knuth; Peter C. Richardson; James H. Monroe

[57] ABSTRACT

A process for immobilizing enzyme-containing microbial cells by contacting such cells with an aqueous agar solution containing from about 1.0 to 8.0% sulfate moiety on a weight/weight basis, contacting a solution of inorganic sodium salts with a stream of the cell mixture whereby agar fibers containing cells are formed; and recovering the cell-containing agar fibers produced.

14 Claims, No Drawings

IMMOBILIZATION OF CATALYTICALLY ACTIVE MICROORGANISMS IN AGAR GEL FIBERS

BACKGROUND OF THE INVENTION

The use of immobilized enzyme catalysts either "as is" or in their intracellular form has become an integral aspect of industrial chemical production. Immobilized catalysts have been developed for the production of many chemical and food products, and include enzymic systems such as aspartase, penicillin acylase, glucose isomerase, beta-galactosidase, alpha-amylase, and amino acylase. The immobilization of such catalysts has generally included methods such as entrapment within cross-linked gels; encapsulation within hollow fibers/macro-capsules; adsorption on inert supports/ion-exchange resins; cross-linking by multifunctional reagents; and covalent binding to polymeric supports. Examples of these various methods and their application abound in the literature and review articles (e.g. *Applied Biochemistry and Bioengineering,* Vol. 1, Immobilized Enzyme Principles) and will not be discussed here. Industrial applications of these various methods have had to focus on the feasibility of the selected support matrix for large-scale operations. It is particularly important for industrial applications that the matrix have good mechanical stability and good hydrodynamic properties such that compression, compaction, and/or breaking of the support does not occur upon extended use. The support must also be of suitable permeability and surface area and of such a structure that immobilized catalyst activity is maximized and diffusional resistances are minimized.

In answer to these requirements, Chibata et al (U.S. Pat. No. 3,791,926) have developed various methods of entrapping enzymes/microorganisms within synthetic-type polymer matrices (e.g. polyacrylamide), particularly for the production of aspartic acid. Nelson (U.S. Pat. No. 3,957,580) has similarly reported a method of entrapping/cross-linking enzyme-containing microbial cells within other types of synthetic polymer systems in which the immobilized cells are further cross-linked to the polymer matrix by poly-functional reagents such as glutaraldehyde. Synthetic polymer systems of these types have two major drawbacks: (1) the preparation of the immobilized catalyst can involve the use of toxic irritants (monomers, initiators, cross-linkers, etc.) which would present problems in the production of food-grade products; and (2) the support matrix can deform/or compact upon extended use in a large-scale column reactor system.

To improve the characteristics of gel-entrapped immobilized catalysts, Chibata et al have investigated the use of sulfated polysaccharide gels (such as kappa-carrageenan) as a support matrix (U.S. Pat. No. 4,138,292). These types of gels can be used in a variety of configurations (beads, membranes, etc.) for the immobilization of enzymes and microorganisms. The limitation in these applications is that the polysaccharide must contain 10% (w/w) sulfate moiety, and that a gel-hardening reagent (e.g. a water-soluble organic amine or a metal ion of atomic weight greater than 24) must be used to ensure a stable gel support. Previous literature reports have indicated that microorganisms entrapped with an agar gel matrix (Japan Patent Application No. 95470/1975) did not retain the gel shape, particularly at temperatures above 40° C., and was transformed into a "sol" structure. Similarly, carageenan exhibits this same loss of form/structure unless gel-hardening reagents of the type mentioned above are employed to retain mechanical stability. I have now found that stable, catalytically active systems can be obtained using an agar gel containing less than 10% (w/w) sulfate moiety which does not require any of the previously used gel-hardening reagents. Furthermore, this type of system can be used in the form of a "fiber catalyst" in a column reactor and not lose its shape. The illustrative example with this newly developed immobilization process utilizes an aspartase-containing microorganism which is used as an immobilized cell column reactor for the continuous-flow production of L-aspartic acid from an ammonium fumarate substrate. The interest in this particular immobilized cell system has to do with the importance of L-aspartic acid itself, which is used as a food-grade product and as an intermediate in the production of other food-grade products. Industrial production of aspartic acid has generally involved either batch-fermentation methods in which aspartase-containing microorganisms are used to carry out the reaction and are then discarded after a single use, or have involved the use of immobilized aspartase-containing microorganisms which may be used repeatedly in a continuous-flow mode of operation. Due to the reduced labor costs and reuseable form of the catalyst associated with the latter method, it is generally favored over the batch-type systems provided that a suitably designed (good activity, stability, etc.) immobilized cell catalyst is available. The present invention does allow the production of such an immobilized cell derived catalyst.

The methodology employed in this invention is adaptable for other immobilized cell processes (e.g. penicillin acylase systems), and also to native enzyme immobilization: the exact application(s) will depend on the requirements of the practitioner of the invention.

SUMMARY

This invention relates to immobilized enzyme-containing microbial cells and to a process of preparing same in which the immobilization is effected by means of entrapping whole cell enzymes in fibrous particles of agar gel. The resultant fibers can then be used in a suitably designed reactor for the continuous flow production of product.

The invention comprises a process for immobilizing enzyme-containing microbial cells comprising:
  (a) contacting said cells with an aqueous agar solution at a temperature of from about 40° C. to 60° C.; said agar containing from about 1.0 to 8.0% sulfate moiety on a weight/weight basis;
  (b) contacting a 0.10 to 5.0 molar solution of inorganic sodium salts at a temperature of from about 0° C. to 20° C. with a stream of the mixture formed in a) above whereby agar fibers containing cells are formed; and
  (c) recovering said cell-containing agar fibers.

The process is preferred wherein:
  (a) said agar contains from 2.0 to 3.0% sulfate moiety on a weight/weight basis;
  (b) said inorganic sodium salt solution is a 3.0 to 5.0 molar solution of sodium chloride; and
  (c) said contacting of mixtures 1a) and 1b) is conducted at a temperature of from about 5° to 15° C.

The process is preferred wherein said microbial cells contain the enzyme aspartase (aspartate ammonia-lyase), penicillin acylase, glucose isomerase, glucose oxidase, fumarase, invertase, cis-trans maleic isomerase, or L-aspartate beta-decarboxylase. The process is also preferred wherein the aspartase containing microbial cells are of the species Bacillus megaterium and, alternatively, wherein the cells are contacted with a 0.1 to 2.0 molar solution of fumarate or aspartate ion at a temperature of from 15° to 45° C. prior to further processing of the cells. The process is further preferred wherein the cell-containing agar fibers are contacted with a 0.1 to 2.0 molar solution of ammonium fumarate at a pH of from 8.0 to 9.5 and at a temperature of from about 25° C. to 55° C.

The process is also preferred wherein penicillin acylase containing microbial cells are of the species Proteus rettgeri.

DETAILED DESCRIPTION OF THE INVENTION

In preparing the product of this invention, enzyme-containing microbial cells are entrapped within a fibrous agar matrix. Agar itself is a natural polysaccharide complex extracted from various genera of agar-producing algae. Structurally agar is considered to be a complex mixture of alternating alpha (1-3) and beta (1-4) linked polysaccharides containing various levels of sulfate moiety. The particular composition of the agar used in this invention contains from 1-8%, preferably 2-3%, and most preferably about 2.54% (w/w) sulfate moiety, and also typically contains (% w/w): 0.13% calcium, 0.01% barium; 0.19% silica; 0.43% chloride; and 0.17% nitrogen. It is important to note that the sulfate composition of the agar used in this invention is less than the 10% (or greater) sulfate moiety used in prior polysaccharide-type preparations of other investigators.

The unique property of agar which allows it to be used as a mechanically stable support matrix is its ability to form an aqueous colloidal "sol" at high temperature which, upon cooling, is transformed into a gel network that does not revert back to the sol form under temperatures used for most enzymatic reactions.

The aspartase-containing microbial cells used to demonstrate this invention were Bacillus megaterium; these cells can be pre-treated with fumaric acid or aspartic acid (prior to gel entrapment) to increase the observed intracellular aspartase activity. The fibrous agar particles of entrapped aspartase-containing B. megaterium cells are typically from 1.9 to 3.7 cm in length and from 0.1 to 0.2 cm in width. (The size of the agar fibers formed can be varied by changing the processing conditions.) The fibrous agar-entrapped cells are used for the continuous flow production of L-aspartic acid from a 1.5 molar ammonium fumarate feed stream. Optimal reactor conditions include a pH range of from 8.5-9.0; a temperature range of from 37° C.-45° C.; and a (preferred) upflow feed application at from 1.5-3.0 bed volumes per hour required to attain the ≧98% molar conversion yield level. The reactor column may be operated continuously without affecting the hydrodynamic properties of the system. Immobilized whole cell aspartase activity incorporation is typically 70%-100% that of free whole cell activity, with catalyst half-life of at least 132 days and as high as 277 days. Following are more detailed aspects of the methodology of the invention and its application again using whole-cell aspartase as the illustrative example.

In a typical experiment, the agar used was obtained as a dried extract from Difco laboratories (of Detroit, MI) and contained 2.54% (w/w) sulfate moiety. It was dissolved in 90° C.-100° C. water (w/stirring) to give a 5% colloidal sol of aqueous agar. After formation of this sol, the temperature was reduced to 45° C.-60° C. prior to introduction of the aspartase-containing whole cells. If the temperature of the sol is allowed to drop below 45° C. the agar sol may gel. Temperatures much above 60° C. should be avoided due to the possibility of thermal denaturation of the intracellular enzyme when the whole cells are added to the agar sol. The aspartase-containing Bacillus megaterium organism used was obtained as a concentrated cell paste/slurry by centrifugation. This cell paste/slurry may be mixed with from a 0.25 to 0.50 parts by volume of water to 1.0 parts by weight of cell (wet) in order to establish a more easily workable cell mass. At this point the aspartase-containing B. megaterium cells optionally can be incubated with a 1.5 molar solution of ammonium fumarate substrate. The use of 0.5 parts by weight of (wet) cell paste/slurry to 1.0 parts by volume of this substrate, held at 25° C. for 12-16 hours, can result in up to a 3-fold increase in observed intracellular aspartase activity. Retention of this observed activity increase upon immobilization allows the design of a reactor system of optimal productivity.

The cell paste/slurry (pre-treated or not) should then be heated to 45° C. (with stirring) prior to mixing with the agar sol. The cell paste/slurry is then added in a ratio of from 0.25-0.75 parts by (wet) weight of cells to 1.0 parts by volume of the 5% agar sol (with stirring). The temperature is maintained at from 45° C.-60° C. during the mixing step to prevent gelation from occurring. The homogeneous cell/agar mixture is then pumped at a rate of from 1.0 to 12.0 l/hr through a 0.125 inch diameter nozzle into a stirred, 0.10 molar to 5.0 molar inorganic sodium salt solution maintained at 10° C.-15° C. One part by volume of the cell/agar mixture is pumped into 4.0 parts by volume of the cold salt solution at such a rate as to maintain a continuous stream of addition of the agar/cell mixture. Formation of the agar-entrapped immobilized cell fibers then forms immediately upon contacting the surface of the stirred saline solution. After all of the agar/cell mixture has been added to the salt solution, the catalyst fibers may be collected by vacuum filtration over a Lapp-filter and washed with 1.0-2.0 volumes of water. The weight of wet cells in the catalyst fibers will range from 30-40% that of the overall (wet) catalyst weight. The catalyst fibers should then be held in a 1.5 molar solution of ammonium fumarate substrate until ready for use in a packed-bed column reactor.

The design of the immobilized-cell column reactor is such that L-aspartic acid production is optimized. Optimal catalyst loading is typically 0.7 parts by weight (wet) catalyst fibers to 1.0 parts by volume of reactor space. The 1.5 molar ammonium fumarate substrate feed is passed over the column at from 1.5-3.0 bed volumes (of column) per hour, at a pH of from 8.5-9.0, and at a temperature of from 37° C.-45° C. L-aspartic acid molar yields of 98+% are typically obtained in a well-designed column reactor. The product may be directly precipitated from the column eluate stream by continuous crystallization; i.e., by adjusting the pH of the eluate stream to 3.2 with sulfuric acid and allowing the resultant L-aspartic acid crystals to granulate for one-half hour.

This invention is equally applicable for a variety of enzyme systems. For example, penicillin acylase, glucose isomerase, glucose oxidase, fumarase, invertase, cis-trans maleic isomerase, and L-aspartate beta-decarboxylase, among others, can all be prepared by the process of this invention. When penicillin acylase is desired, cells of *Proteus rettgeri* can be employed. When immobilization of cells containing glucose isomerase, glucose oxidase, fumarase, invertase, cis-trans maleic isomerase, or L-aspartate beta-decarboxylase (among others) is desired, micro-organisms which may be used can include those of the genera *Streptomyces, Bacillus, Acetobacter, Pseudomonas,* and *Aspergillus*. Micro-organisms of this type may not necessarily be intact living cells, but may be physically or chemically treated prior to use in the present invention. It will also be possible to entrap extracellular or native enzymes in agar fibers by the process of this invention.

Specifics of the above methodology are presented in the following Examples.

EXAMPLE 1

A *Bacillus megaterium* fermentation broth grown under aerobic conditions at 28° C. and pH 8.5 for 18 hours on an NZ Amine B and a corn steep liquor substrate was centrifuged at 15,000 x g for 15 min. The cell spindown (wet) weight was 34.7 gms per liter of fermentation broth. Prior to immobilization of the cells, 56.0 gms of the wet cells were held in approximately 100 mls of 1.5 molar ammonium fumarate for 16 hours at 25° C. This suspension was then collected by centrifugation at 15,000 x g for 15 min: wet cell yield was 38.0 gms (i.e. a 32% wet weight loss of cells occurred upon incubation in the ammonium-fumarate substrate). The aspartase activity of these treated cells was approximately 5.17 gms of L-aspartic acid produced per hour per gm of wet cell.

To 63 mls of 90° C.-95° C. water, 3.3 gms of Bacto-Agar (from Difco Laboratories, Detroit, MI) were added and the mixture stirred at 90° C.-95° C. until a colloidal sol had formed. This sol was then slowly cooled to 55° C.-60° C. with stirring; the viscosity of the 5% agar sol (at 55° C.) was 640 centipoise.

To 35.0 gms of the treated *B. megaterium* cells were added 9.0 mls of water; the cell slurry was heated to 45°-50° C., with stirring. This heated cell slurry was then added to the 5% agar sol with stirring and at a temperature maintained above 50° C. The cell-agar suspension was well mixed to ensure uniform distribution of cells throughout.

The cell-agar suspension was maintained at 55° C. and pumped at a rate of approximately 1.0 l/hr. through a 0.125 inch diameter nozzle into 440 mls of a stirred, 3.0 molar sodium chloride solution maintained at 10°-15° C. Agar-entrapped fibers of immobilized aspartase-containing *B. megaterium* cells were formed immediately upon contact of the agar-cell suspension with the surface of the cold saline solution. The immobilized cell fibers were collected by filtration on Lapp-Filter and washed with water. Wet weight of the catalyst fibers was 106 gms, of which approximately 33% (35.0 gms) were immobilized *B. megaterium* cells.

The aspartase activity of the catalyst fibers was approximately 1.68 gms of L-aspartic acid produced per hour per gm of gel, or 5.08 gms of L-aspartic acid produced per hour per gm of (wet) immobilized cell. Activity retention in the agar-catalyst fibers was therefore 98.2% that of the treated, non-immobilized whole cell.

The catalyst fibers were held in ammonium-fumarate substrate until used in a column reactor.

EXAMPLE 2

Ninety-five (95) gms of the aspartase-containing catalyst fibers prepared in Example 1 were packed into a 147 ml (2.5 cm X 30 cm) jacketed glass column. Water maintained at 45° C. was circulated through the jacket of the column and was also used to pre-heat the 1.5 molar ammonium-fumarate substrate solution (containing 1.0 milli-molar Mg++ ion). The pre-heated substrate feed was pumped (downflow) through the column at 7.35 mls/min (3.0 bed volumes/hr) and the eluate collected: HPLC analysis of the eluate indicated that L-aspartic acid was produced in 98.3% molar yield. The L-aspartic acid product was recovered by pH adjustment (to 3.2) of the eluate with 58% sulfuric acid. Recovery yields ranged from 84% to 94% (dry weight) dependent on the crystallization and granulation temperatures, which ranged from 45° C. to 25° C.

EXAMPLE 3

A culture of *Proteus rettgeri* [ATCC 31052 (ATCC 9250)] grown under aerobic conditions at 28° C. and pH 6.8-7.0 on a glucose substrate was centrifuged and the separated cells washed with water. Fifty (50) wet grams of the washed cells were mixed with 25 mls of water, and the cell slurry was heated to 45° C. One hundred (100) mls of an aqueous 5% agar solution (Bacto-agar from Difco) was prepared at 95° C. and then cooled to 55° C. The pre-heated *P. rettgeri* cell slurry was mixed with the agar solution and the temperature was maintained at 55° C. The agar/cell slurry was then pumped (at 1.0 l/hr. through a 0.125 inch feed tube into 700 mls of a stirred 3.0 M aqueous sodium chloride solution maintained at 5°-10° C. Agar-entrapped fibers of penicillin-acrylase containing *P.rettgeri* cells were formed immediately upon contact of the agar-cell slurry with the saline solution. The wet weight of the fibers was 173 gms.

Penicillin acylase activity studies were made on the fiber catalyst in which 22.8 gms of the fibers were packed into a (5.6 cm X 3.3 cm) cylindrical glass reactor. The temperature of the reactor was maintained at 37° C., and 1.0 liter of 10%(w/v) potassium peni-cillin G (pH 8.0) was pre-heated to 37° C. and recycled thru the reactor at a flow rate of 22.1-48.7 bed volumes/hr (29.9-65.9 mls/min). Ammonium hydroxide (1.0 N) was added to the recycled Penicillin G substrate to maintain a pH of 8.0, and the reaction progress followed by monitoring the amount of ammonium hydroxide added and by HPLC analysis of residual penicillin G: conversion yields of 19% were obtained after 3 hrs of reactor operation.

I claim:
1. A process for immobilizing enzyme-containing microbial cells comprising:
 (a) contacting enzyme-containing microbial cells with an aqueous agar solution at a temperature of from about 40° to 60° C.; said agar containing from about 1.0 to 8.0% sulfate moiety on a weight/weight basis;
 (b) contacting a 0.10 to 5.0 molar solution of inorganic sodium salts at a temperature of from about 0° to 20° C. with a stream of the mixture formed in a) above whereby agar fibers containing cells are formed; and
 (c) recovering said cell-containing agar fibers.

2. The process of claim 1 wherein:
(a) said agar preferably contains from 2.0 to 3.0% sulfate moiety on a weight/weight basis;
(b) said inorganic sodium salt solution is preferably a 3.0 to 5.0 molar solution of sodium chloride; and
(c) said contacting of mixtures 1a) and 1b) is at a temperature of 5° to 15° C.

3. The process of claim 1 wherein said microbial cells contain the enzyme aspartase (aspartate ammonia-lyase).

4. The process of claim 1 wherein said microbial cells contain the enzyme penicillin acylase.

5. The process of claim 1 wherein said microbial cells contain the enzyme glucose isomerase.

6. The process of claim 1 wherein said microbial cells contain the enzyme glucose oxidase.

7. The process of claim 1 wherein said microbial cells contain the enzyme fumarase.

8. The process of claim 1 wherein said microbial cells contain the enzyme invertase.

9. The process of claim 1 wherein said microbial cells contain the enzyme cis-trans maleic isomerase.

10. The process of claim 1 wherein said microbial cells contain the enzyme L-aspartate beta-decarboxylase.

11. The process of claim 3 wherein said aspartase containing microbial cells are of the species *Bacillus megaterium*.

12. The process of claim 4 wherein said penicillin acylase containing microbial cells are of the species *Proteus rettgeri*.

13. The process of claim 11 wherein said aspartase containing cells of the species *Bacillus megaterium* are contacted with a 0.1 to 2.0 molar solution of fumarate or aspartate ion at a temperature of from 15° to 45° C. prior to gel entrapment of said cells.

14. The process of claim 13 wherein the cell-containing agar fibers are contacted with a 0.1 to 2.0 molar solution of ammonium fumarate at a pH of from 8.0 to 9.5 and at a temperature of from about 25° to 55° C.

* * * * *